United States Patent [19]

Delmonte et al.

[11] 4,237,935
[45] Dec. 9, 1980

[54] HYDRAULIC PRESSURE RELIEF VALVE AND FLUID ISOLATOR

[75] Inventors: Julian Delmonte, La Canada; M. Janet Kirkwood, Montebello; Douglas G. Ritchie, Pasadena, all of Calif.

[73] Assignee: Eaton Corporation, Cleveland, Ohio

[21] Appl. No.: 969,609

[22] Filed: Dec. 14, 1978

[51] Int. Cl.³ .............................................. F16K 15/14
[52] U.S. Cl. ..................................... 137/860; 128/675
[58] Field of Search .................. 73/706; 128/673, 675, 128/748; 137/853, 860

[56] References Cited

U.S. PATENT DOCUMENTS

| | | | |
|---|---|---|---|
| 2,473,912 | 6/1949 | Schwinn | 137/853 |
| 3,865,100 | 2/1975 | Kanai | 128/675 |
| 4,030,497 | 6/1977 | Binard | 128/675 X |
| 4,072,056 | 2/1978 | Lee | 128/675 X |

FOREIGN PATENT DOCUMENTS 6611202  2/1968  Netherlands ............................ 137/860

Primary Examiner—Robert G. Nilson
Attorney, Agent, or Firm—Kevin Redmond

[57] ABSTRACT

A body of electrically insulating material contains a passageway extending completely through the body. The passageway includes a flexible diaphragm dividing the passageway into two compartments to isolate a transducer placed on one side of the diaphragm from direct contact with fluid contained on the opposite side. A pressure relief port, passing from one side of the body to the passageway on the fluid side of the diaphragm, is covered with an "O" ring. Excessive fluid pressure forces the "O" ring away from the relief port to vent the pressure and thereby prevent damaging the transducer.

1 Claim, 2 Drawing Figures

HYDRAULIC PRESSURE RELIEF VALVE AND FLUID ISOLATOR

BACKGROUND

1. Field

This invention relates to the protection of medical transducers and, in particular, to the establishment of electrical, over-pressure, and sanitary isolation between transducers and patients.

2. Prior Art

Medical transducers are sensing devices, usually connected to patients by way of a tube referred to as a catheter. One end of the catheter may be attached to or inserted into the patient. The catheter contains a fluid which transmits pressure signals from the patient to the transducer.

A number of problems are present in this type of patient monitoring system. Air bubbles within the fluid diminish the transmission of the pressure signals. The patient may be subject to electrical shock because of a current flowing from the transducer to the patient by way of the fluid in the catheter. Microorganisms may also pass from the transducer to the patient through the catheter fluid.

To overcome these problems, attempts have been made to sanitize the transducer and flush the catheter with a device, such as a syringe. Sensitive transducers were often damaged by the handling required in these operations and by the high pressure produced by the syringe. To prevent electrical shock, reliance was placed on electrically isolating the surface of the transducer; however, an internal short, which might not be readily detected, could result in electrical shock.

SUMMARY

Electrical, over-pressure and sanitary isolation between the fluid in a catheter and a transducer is provided by means of the present invention. The invention comprises an insulating body with a passageway divided by a diaphram. The catheter is connected to one end of the passageway, while the transducer is connected to or inserted within the passageway at the opposite end. Pressure signals from fluid within the catheter are transmitted through the diaphram to the transducer. The diaphram and insulating body provide the electrical and sanitary isolation. Over-pressure protection is provided by an over-pressure relief port located on the fluid side of the diaphram.

DETAILED DESCRIPTION OF THE INVENTION

Figure 1:
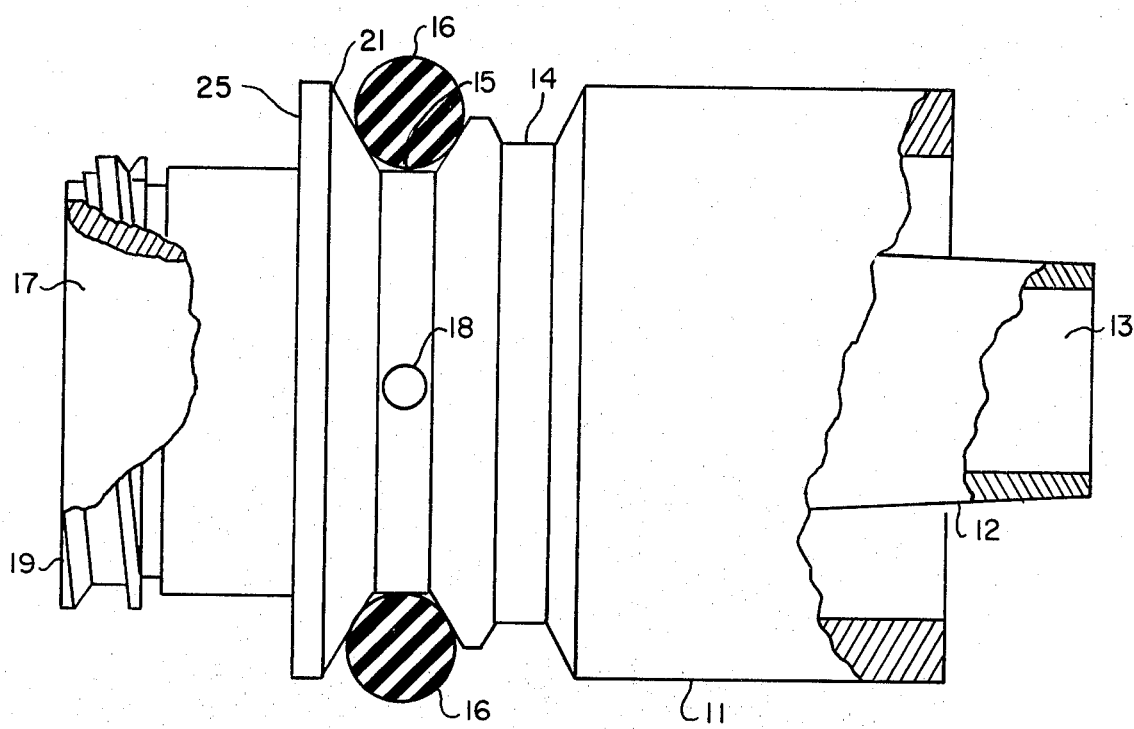
FIG. 1 is broken away side view of the present invention.

Referring to FIG. 1, a body 11 contains a passageway which extends through the device. The right end of the passageway is indicated by drawing numeral 13, while the left end is indicated by drawing numeral 17. The left end of the body includes threads 19 adapted to accept and secure a transducer. The right end is in the form of a conical projection 12 designed to accept and secure a catheter. About the central region of the body are two grooves, 15 and 14, which encircle the device. In the left hand groove is a relief port 18 which extends through the body to the passageway. An "O" ring 16, shown in cross section in FIG. 1, is normally seated in the groove 15 where it covers port 18. The "O" ring may be forced into groove 14 to leave port 18 uncovered, if desired.

Figure 2:
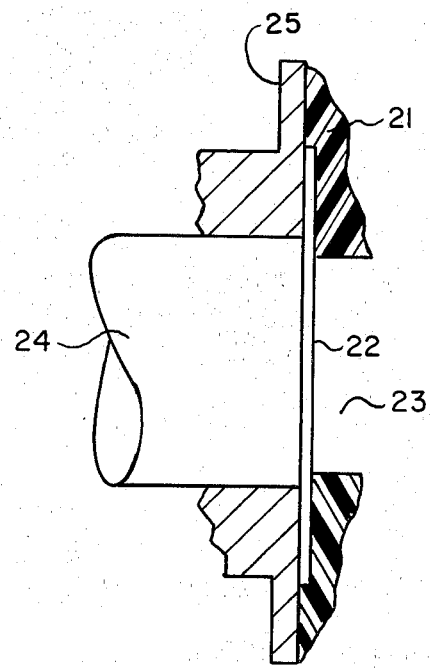
FIG. 2 is a partial cross sectional view of the device of FIG. 1 showing the location of the diaphram.

Referring to FIG. 2, a portion of the body 21 contains a portion of the passageway 23. Another portion of the body 25 located adjacent portion 21 contains a shoulder. Across the passageway is a diaphram 22 which divides the passageway into two compartments. In the left compartment is a transducer 24 in contact with the diaphram 22.

In the operation of the present invention, a catheter containing fluid is connected to the conical projection 12, while a transducer is secured to the opposite end of the device by means of threads 19. Pressure signals in the catheter fluid are transmitted through the diaphram to the transducer. Prior to connecting the catheter to the device, it is filled with fluid, as is one compartment of the passageway 13, by way of the conical projection 12. Excessive fluid is bled from the relief port 18 by temporarily lifting the "O" ring to insure that the fluid compartment of the device is completely filled with fluid and all air has been ejected. The "O" ring is replaced to close the relief port. The catheter is then connected to the conical projection. Any excessive fluid in the system occurring during the connection step forces the "O" ring away from port 18 and is released.

In the event that the catheter is flushed or for other reasons the pressure of the fluid is raised above a specific level, such as 10 pounds per square inch, fluid is released through the relief port in a similar manner to prevent over-pressure from being applied to the transducer.

Electrical and sanitary isolation between the transducer and the catheter is provided by the insulating body and the diaphram.

The present invention may be made either of disposable materials and replaced for each application to a patient or may be reused if fabricated from materials designed to sustain sanitizing operations.

Having described our invention, we claim:

1. A hydraulic pressure release valve and isolator, comprising:
   (a) a body, having a passageway extending completely through said body,
   (b) a flexible diaphram secured to said body within said passageway and extending completely across said passageway in a generally transversal direction to prevent flow through said passageway,
   (c) a port extending from the outside of said body to said passageway, located to one side of said diaphram,
   (d) means for closing said port below a specified pressure within said port and removing said closure above said specified pressure,
   said body being fabricated of electrically insulating material and further comprises a threaded end about one end of said passageway to accept a sensing device and a hollow conical projection at the other end of said passageway to accept a flexible tube, said conical projection being located on the same side of said diaphram as said port to transmit pressure from within a tube connected to said conical portion through said diaphram to said sensing device, said means for closing said port is an "O" ring of resilient material surrounding said body and covering said port, and said body contains a first groove encircling the body and passing through the opening of said port to hold said "O" ring in place over said port opening and said body contains a second groove encircling the body adjacent said first groove to hold said "O" ring away from said port and thereby uncover said port.

* * * * *